(12) United States Patent
Bennett et al.

(10) Patent No.: US 8,206,053 B2
(45) Date of Patent: Jun. 26, 2012

(54) DEVICE THAT CAN BE ASSEMBLED BY COUPLING

(75) Inventors: Richard Bennett, Cooper City, FL (US); Hyosig Kang, Weston, FL (US); Brian Schmitz, Fort Lauderdale, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 278 days.

(21) Appl. No.: 12/644,964

(22) Filed: Dec. 22, 2009

(65) Prior Publication Data

US 2010/0166496 A1  Jul. 1, 2010

Related U.S. Application Data

(60) Provisional application No. 61/203,475, filed on Dec. 23, 2008.

(51) Int. Cl.
*B25B 11/00* (2006.01)
(52) U.S. Cl. ............................ 403/59; 403/121; 29/281.1
(58) Field of Classification Search .................... 403/13, 403/59, 121; 29/281.1; 269/71, 45, 55
See application file for complete search history.

(56) References Cited

U.S. PATENT DOCUMENTS

| 3,353,771 | A | * | 11/1967 | Te Bow | 248/662 |
| 4,290,574 | A | * | 9/1981 | Archibald | 248/177.1 |
| 4,360,974 | A | * | 11/1982 | de Cuissart | 33/645 |
| 4,541,178 | A | * | 9/1985 | White | 33/645 |
| 4,610,020 | A | * | 9/1986 | La Fiandra | 378/35 |
| 4,770,497 | A | * | 9/1988 | Brown | 359/896 |
| 5,046,375 | A | | 9/1991 | Salisbury et al. | |
| 5,161,424 | A | | 11/1992 | Saberton et al. | |
| 5,167,464 | A | * | 12/1992 | Voellmer | 403/13 |
| 5,207,114 | A | | 5/1993 | Salisbury et al. | |
| 5,513,946 | A | | 5/1996 | Sawada et al. | |
| 5,778,730 | A | | 7/1998 | Solomon et al. | |
| 5,794,487 | A | | 8/1998 | Solomon et al. | |
| 5,816,770 | A | | 10/1998 | Itagaki | |

(Continued)

FOREIGN PATENT DOCUMENTS

EP  1 815 949 A1  8/2007

(Continued)

OTHER PUBLICATIONS

International Search Report corresponding to PCT/US2009/069231, dated Mar. 22, 2010, 4 pages.

(Continued)

*Primary Examiner* — Joshua Kennedy
(74) *Attorney, Agent, or Firm* — Foley & Lardner LLP (57) ABSTRACT

A device can be assembled by a coupling. The device includes first and second body members and positioning structure. The first and second body members are designed to be coupled relative to each other. The positioning structure is designed to provide an interface between the first and second body members, and to position the first and second body members relative to each other via first, second, and third contact areas. The first, second, and third contact areas are each substantially linear and are collectively configured to receive loads, and to limit positioning of the first and second body members relative to each other with regard to five degrees of freedom. A fourth contact area between the first and second body members is designed to limit positioning of the first and second body members relative to each other in a sixth degree of freedom, in a first translational direction.

20 Claims, 7 Drawing Sheets

U.S. PATENT DOCUMENTS

| | | | |
|---|---|---|---|
| 6,152,941 | A | 11/2000 | Himes et al. |
| 6,236,788 | B1 * | 5/2001 | Moisel ............................ 385/52 |
| 6,370,974 | B1 | 4/2002 | Jourtchenko et al. |
| 6,394,998 | B1 | 5/2002 | Wallace et al. |
| 6,668,466 | B1 * | 12/2003 | Bieg et al. ........................ 33/503 |
| 6,688,189 | B2 | 2/2004 | Hashimoto et al. |
| 6,729,589 | B2 * | 5/2004 | Shelef ........................ 248/181.1 |
| 6,826,324 | B2 * | 11/2004 | Steinberg et al. ............... 385/16 |
| 7,021,167 | B2 | 4/2006 | Liesegang |
| 7,316,681 | B2 | 1/2008 | Madhani et al. |
| 2002/0035372 | A1 | 3/2002 | Zisterer et al. |
| 2003/0075790 | A1 * | 4/2003 | Steinberg et al. ............. 257/686 |
| 2003/0104886 | A1 | 6/2003 | Gajewski |
| 2003/0152661 | A1 | 8/2003 | Yu et al. |
| 2004/0049205 | A1 | 3/2004 | Lee et al. |
| 2006/0016061 | A1 * | 1/2006 | Shelef ............................ 29/464 |
| 2006/0047272 | A1 | 3/2006 | McPherson et al. |
| 2007/0089557 | A1 | 4/2007 | Solomon et al. |
| 2007/0142969 | A1 | 6/2007 | Devengenzo et al. |
| 2007/0299427 | A1 * | 12/2007 | Yeung et al. ....................... 606/1 |
| 2008/0010706 | A1 | 1/2008 | Moses et al. |
| 2008/0021440 | A1 | 1/2008 | Solomon |
| 2008/0058861 | A1 | 3/2008 | Cooper et al. |
| 2008/0087871 | A1 | 4/2008 | Schena |
| 2008/0248907 | A1 | 10/2008 | Cottrell |
| 2008/0278105 | A1 | 11/2008 | Somes |
| 2008/0287862 | A1 | 11/2008 | Weitzner et al. |
| 2010/0168723 | A1 | 7/2010 | Suarez et al. |
| 2010/0170361 | A1 | 7/2010 | Bennett et al. |
| 2010/0170362 | A1 | 7/2010 | Bennett et al. |
| 2011/0174097 | A1 | 7/2011 | Bergamasco et al. |

FOREIGN PATENT DOCUMENTS

| | | |
|---|---|---|
| EP | 1 815 950 A1 | 8/2007 |
| EP | 1 915 966 A1 | 4/2008 |
| WO | WO 2010-074739 | 7/2010 |
| WO | WO 2010-074742 | 7/2010 |
| WO | WO 2010-074744 | 7/2010 |
| WO | WO 2010-075404 | 7/2010 |

OTHER PUBLICATIONS

PCT Written Opinion corresponding to PCT/US2009/069231, dated Mar. 22, 2010, 5 pages.
U.S. Appl. No. 12/654,518, filed Dec. 22, 2009, Bennett et al.
International Search Report mailed May 7, 2010 in PCT/US2009/006655, 4 pages.
International Search Report mailed May 7, 2010 in PCT/US2009/006659, 4 pages.
International Search Report mailed May 7, 2010 in PCT/US2009/006661, 4 pages.
PCT Written Opinion mailed May 7, 2010 in PCT/US2009/006655, 6 pages.
PCT Written Opinion mailed May 7, 2010 in PCT/US2009/006659, 6 pages.
PCT Written Opinion mailed May 7, 2010 in PCT/US2009/006661, 6 pages.

* cited by examiner

DEVICE THAT CAN BE ASSEMBLED BY COUPLING

CROSS-REFERENCE TO RELATED PATENT APPLICATIONS

This application claims priority to U.S. Provisional Patent Application Ser. No. 61/203,475, filed on Dec. 23, 2008, which is hereby incorporated by reference in its entirety.

BACKGROUND

1. Field of Invention

The present disclosure relates generally to the field of devices that can be assembled by coupling. As a more specific example, the present disclosure relates to devices that can be assembled by coupling to connect an end effector to a robotic arm of a robotic surgical system.

2. Description of Related Art

A robotic surgical system may perform surgical tasks, including providing haptic feedback or maneuvering a surgical tool to, for example, assist in removing tissue (e.g., bone) or producing an incision. The surgical tool can be attached to an end effector that is coupled to a mount on an arm of the robotic surgical system.

Because of the precision generally required for surgical tasks, a control system (e.g., a computer aided navigation system) of the robotic surgical system is designed to operate with highly accurate positional information of the tool. As such, during assembly of the robotic surgical system, the end effector and its mount on the robotic arm are assembled as a calibrated pair using specialized calibration equipment to achieve a high degree of precision and repeatability when mounting the end effector to the robotic arm, which may be a time-consuming and laborious process, even for specialists. Additionally, because the end effector and mount are calibrated together, they must be used as a pair. Thus, the end effector and mount lack interchangeability, meaning that the end effector cannot be reliably coupled to other mounts and vice versa.

During use of the robotic surgical system, it may be necessary to remove and later re-couple the end effector to the robotic arm or to replace the original end effector with a new end effector. When the original end effector is re-coupled to the robotic arm or the new end effector is attached to the robotic arm, it is necessary to achieve a degree of positional accuracy and load carrying ability that are sufficient for proper operation of the robotic surgical system.

SUMMARY

An embodiment of the invention relates to a device that can be assembled by coupling. The device includes first and second body members and positioning structure. The first and second body members are designed to be coupled relative to each other. The positioning structure is designed to provide an interface between the first and second body members, and to position the first and second body members relative to each other via first, second, and third contact areas. The first, second, and third contact areas are each substantially linear and are collectively designed to receive loads, and to limit positioning of the first and second body members relative to each other with regard to five degrees of freedom. A fourth contact area between the first and second body members is designed to limit positioning of the first and second body members relative to each other in a sixth degree of freedom, in a first translational direction.

Another embodiment of the invention relates to a device that can be assembled by coupling. The device includes first and second body members and positioning structure. The first and second body members are designed to be fastened relative to each other. The positioning structure is designed to provide an interface between the first and second body members, and to limit the position of the first and second body members relative to each other in six degrees of freedom. The positioning structure includes a first projection, a second projection, and a third projection. The first projection is on one of the first and second body members, and corresponding first and second surfaces are on the other of the first and second body members. Contacts between the first projection and the first and second surfaces at least partially define first and second contact areas that each are substantially linear. The second projection is on the one of the first and second body members, and a corresponding third surface is on the other of the first and second body members. Contact between the second projection and the third surface at least partially defines a third contact area that is substantially linear. The first and second projections and the first, second, and third surfaces are collectively designed such that the contacts between the first projection and the first and second surfaces and the contact between the second projection and the third surface limit the position of the first and second body members relative to each other in five degrees of freedom. The third projection is on the other of the first and second body members, and a corresponding fourth surface is on the one of the first and second body members. The third projection and the fourth surface are collectively designed such that contact between the third projection and the fourth surface limits positioning of the first and second body members relative to each other in a sixth degree of freedom, in a first translational direction.

Alternative exemplary embodiments relate to other features and combinations of features as may be generally recited in the claims.

BRIEF DESCRIPTION OF THE FIGURES

The accompanying drawings, which are incorporated and constitute a part of this specification, illustrate embodiments of the invention and together with the description serve to explain aspects of the invention.

DETAILED DESCRIPTION

Presently preferred embodiments of the invention are illustrated in the drawings. An effort has been made to use the same or like reference numbers throughout the drawings to refer to the same or like parts.

The present invention relates to a device that can be assembled by coupling. The device can be particularly advantageous in a robotic surgical system. Although this specification describes the device in the environment of a robotic surgical system, it should be understood that the device is applicable to other types of robotic systems, including those used for surgical and non-surgical applications, as well as to non-robotic systems or applications. The present invention is not limited to the details or methodology set forth in the description or illustrated in the figures.

Overview of a Robotic Surgical System

Figure 1:
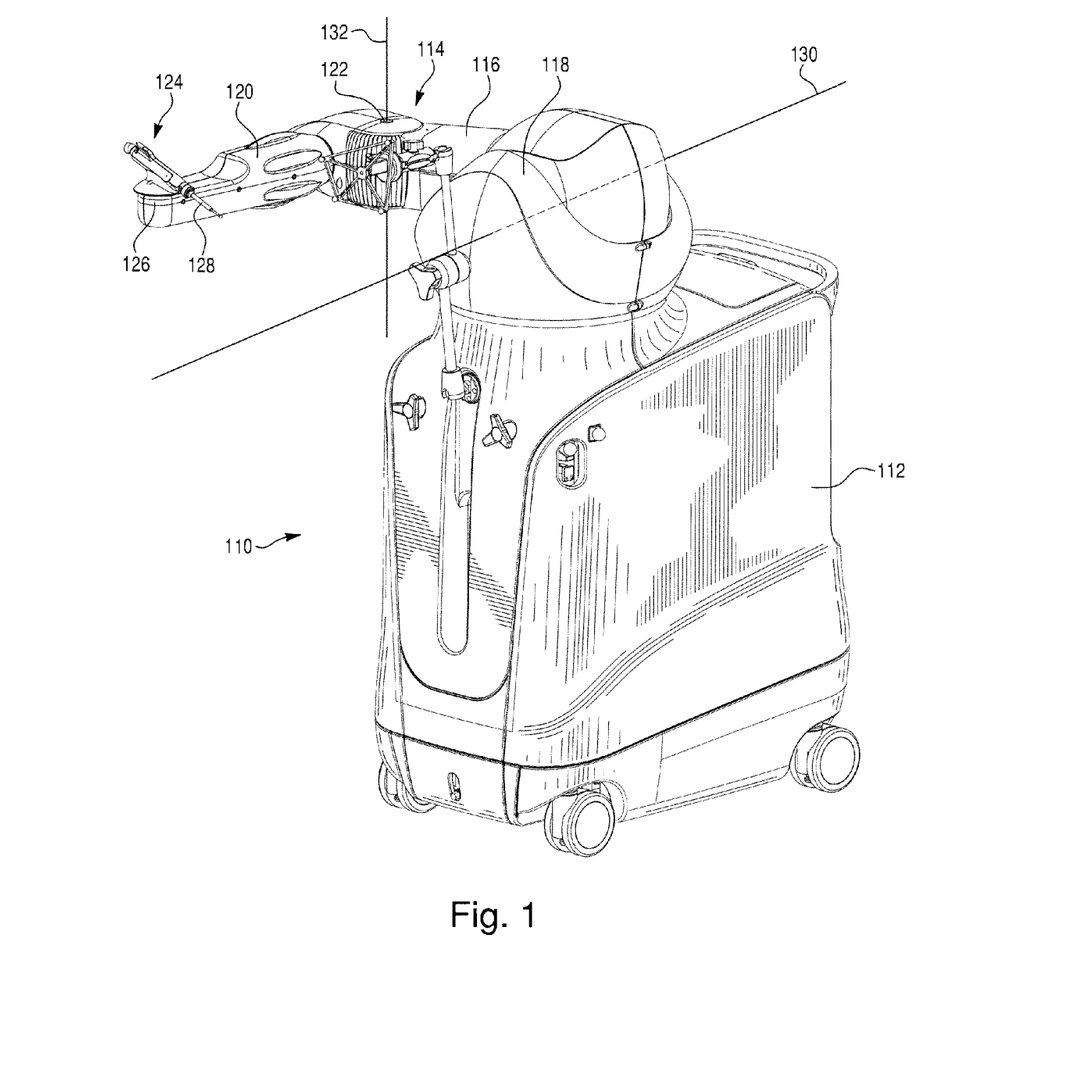
FIG. 1 is a perspective view of an embodiment of a robotic surgical system.
Figure 2:
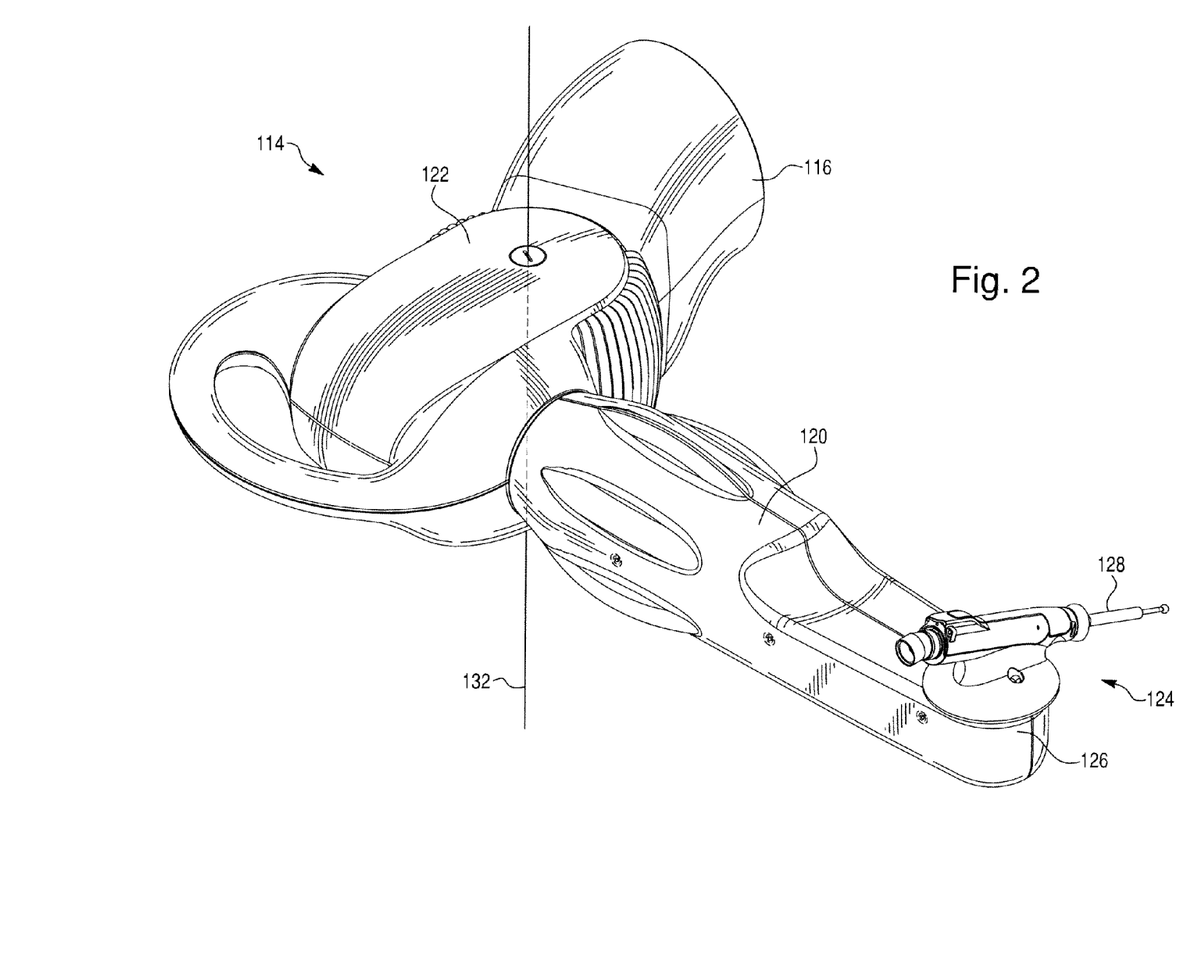
FIG. 2 is a perspective view of an embodiment of a robotic arm of the robotic surgical system of FIG. 1.

FIGS. 1 and 2 illustrate an example of a robotic surgical system 110 in which a device according to the present invention can be used. The robotic surgical system 110 preferably includes a main body 112 upon which is mounted an articulated robotic arm 114 that can be used in an interactive manner by a surgeon to perform a surgical procedure on a patient. In a preferred embodiment, the robotic surgical system 110 is the RIO® Robotic Arm Interactive Orthopedic System manufactured by MAKO Surgical Corp. of Fort Lauderdale, Fla. The robotic arm 114 is preferably a haptic device that works in combination with a computer aided navigation system (not shown) and a tracking device (not shown). For example, as described in U.S. patent application Ser. No. 11/357,197 (Pub. No. US 2006/0142657), filed Feb. 21, 2006, and hereby incorporated by reference herein in its entirety, a surgical tool 128 (such as a cutting burr, a drill, a clamp, scalpel, laser, or other tools) is coupled to the robotic arm 114. The surgeon manually moves the robotic arm 114 to manipulate the surgical tool 128 to perform a surgical task on the patient, such as bone cutting for a joint replacement operation. As the surgeon manipulates the surgical tool 128, the robotic arm can provide haptic (or force) feedback to limit the surgeon's ability to move the surgical tool 128 beyond a predefined virtual cutting boundary, which results in highly accurate and repeatable bone cuts. The robotic arm 114 can work in a passive manner and provide haptic feedback only when the surgeon attempts to cut bone that lies outside the virtual cutting boundary. The haptic feedback can be generated by one or more actuators (e.g., motors; not shown) in the robotic arm and transmitted to the surgeon via a flexible transmission (not shown), such as a tension element transmission. When the robotic arm 114 is not providing haptic feedback, the robotic arm 114 can be freely moveable by the surgeon.

The robotic arm 114 preferably includes a first segment 116 coupled to the main body 112 and maneuverable relative to the main body 112 about a first joint 118 (which may itself be comprised of a plurality of joints to provide multiple degrees of freedom of movement). The robotic arm 114 can further include a second segment 120 coupled to the first segment 116 and maneuverable relative to the first segment 116 about a second joint 122 (which again may be comprised of a plurality of joints to provide multiple degrees of freedom of movement).

The joints 118, 122 may allow for movement of the segments 116, 120 about axes of rotation 130, 132, and more preferably are configured to allow movement about additional axes of rotation. For example, in at least one embodiment the first joint 118 allows for movement of the first segment 116 (and components coupled thereto) relative to the main body 112 at least in a vertical direction about the first axis of rotation 130. The second joint 122 allows for movement of the second segment 120 at least about the second axis of rotation 132 that is orthogonal (e.g., perpendicular, right angled, etc.) to the first axis of rotation 130 (when the robotic arm 114 is in the pose shown in FIG. 1 and when viewed from a position on a line orthogonal to both axes of rotation 130, 132, because the axes of rotation 130, 132 are not coplanar). Preferably the first and second joints 118, 122 are configured to allow movement about additional axes of rotation to increase freedom of movement.

The surgical tool 128 can be positioned relative to the robotic arm 114 by an end effector 124, which can be connected to, for example, a mount 126, which can be connected to the second segment 120 of the robotic arm 114. The degrees of freedom of the robotic arm 114 (e.g., the degrees of freedom provided by the first and second joints 118, 122) provide one or more degrees of freedom of movement of the end effector 124.

The precision with which the end effector 124 positions the surgical tool 128 relative to the robotic arm 114 can be highly important to the operation of the robotic surgical system 110. As mentioned above, the computer aided navigation system can control the actuators to produce haptic feedback for the surgeon. To generate the appropriate haptic feedback, it is important for the computer aided navigation system to know the position in space of the surgical tool 128. A tracking device (not shown) can assist in determining the location in space of the surgical tool 128. For example, the tracking device can be used to identify the location of the main body 112. The position of the robotic arm 114 relative to the main body 112 can then be used to determine the position of the surgical tool 128. To do so, however, it is important to know the spatial relationship between the surgical tool 128 and the robotic arm 114. Thus, in some embodiments, precise coupling of the end effector 124 to the mount 126 on the second segment 120 is needed for the computer aided navigation system to provide accurate haptic feedback. Additionally, the coupling between the end effector 124 and the mount 126 should have sufficient load carrying capability to handle both assembly and operating loads, which include, for example, clamping loads imposed by mechanical fasteners, loads applied when the surgical tool 128 cuts bone, and loads applied as the surgeon exerts force on the end effector 124 and/or the robotic arm 114.

The Device that can be Assembled by Coupling

According to a preferred embodiment, the end effector 124 and the mount 126 can form at least parts of a device 210 that can be assembled by coupling. The device 210 can be, for example, a semi-kinematic coupling that allows for repeated positional accuracy of the placement of the surgical tool 128 relative to the robotic arm 114 and sufficient load carrying ability.

While the device 210 finds particularly advantageous application in the robotic surgical system 110, the device 210 can be used in a variety of different environments. Thus, the device 210 will be more generically described in the context of a first body member 212 (e.g., the end effector 124) and a second body member 216 (e.g., the mount 126), with positioning structure 214, 218 therebetween.

Referring to FIGS. 3-6, an embodiment of the device 210 includes the first body member 212 having positioning structure 214 and the second body member 216 having positioning structure 218 configured to be coupled to the positioning structure 214 of the first body member 212. The positioning structures 214, 218 provide an interface between the first and second body members 212, 216 and position them relative to each other. Preferably, the positioning structures are configured such that the first and second body members 212, 216 can be repeatedly coupled in approximately the same positional relationship, such as approximately the same orientation and position relative to each other. According to an exemplary embodiment the positioning structures 214, 218 may be clamped together and locked relative to each other in substantially six degrees of freedom (three translational and three rotational).

Figure 5:
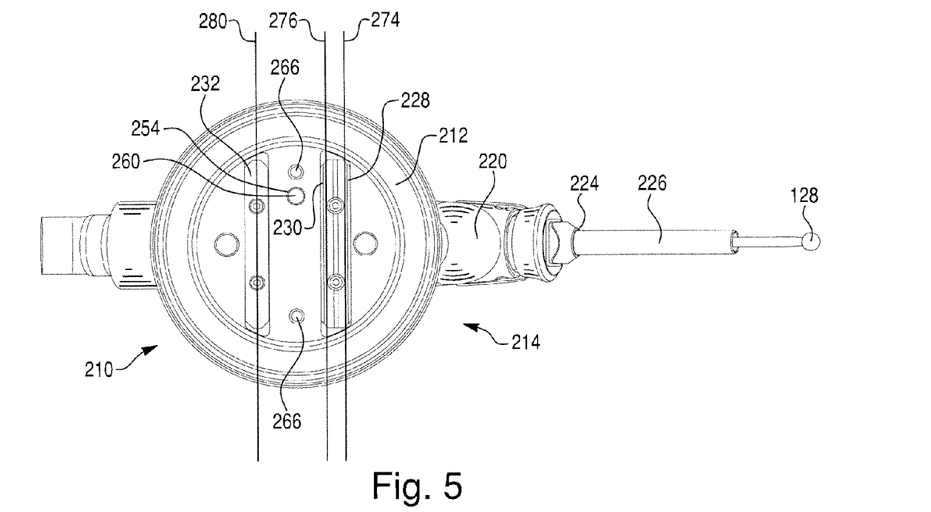
FIG. 5 is a plan view of the first body member of FIG. 3.

The first body member 212 also may include an actuator portion 220 that connects to and drives the tool 128 (see FIG. 5). According to an exemplary embodiment, the actuator portion 220 is rigidly mounted to or integrally formed with the positioning structure 214. The actuator portion 220 can include a port 224 and a drive or electric motor 340 (see FIG. 10), that can be configured to rotate a shaft 226 of the tool 128. In other embodiments, the actuator portion 220 can include an electric solenoid or a vibrating drum (e.g., diaphragm) configured to translate the tool 128 in a reciprocating motion. The tool 128 is locked into the port 224 of the actuator portion 220 or otherwise coupled to the actuator portion 220. In one embodiment, the tool 128 is locked into the port 224 as described in U.S. patent application Ser. No. Unassigned, filed Dec. 22, 2009, entitled "End Effector with Release Actuator," provided attorney docket number 051892-0351, to be filed on the same day as the present application, which is hereby incorporated by reference herein in its entirety. Repeatably accurate coupling of the first body member 212 to the second body member 216 allows the computer aided navigation system to estimate a position of the tool 128, such as relative to a work piece (e.g., patient).

Figure 3:
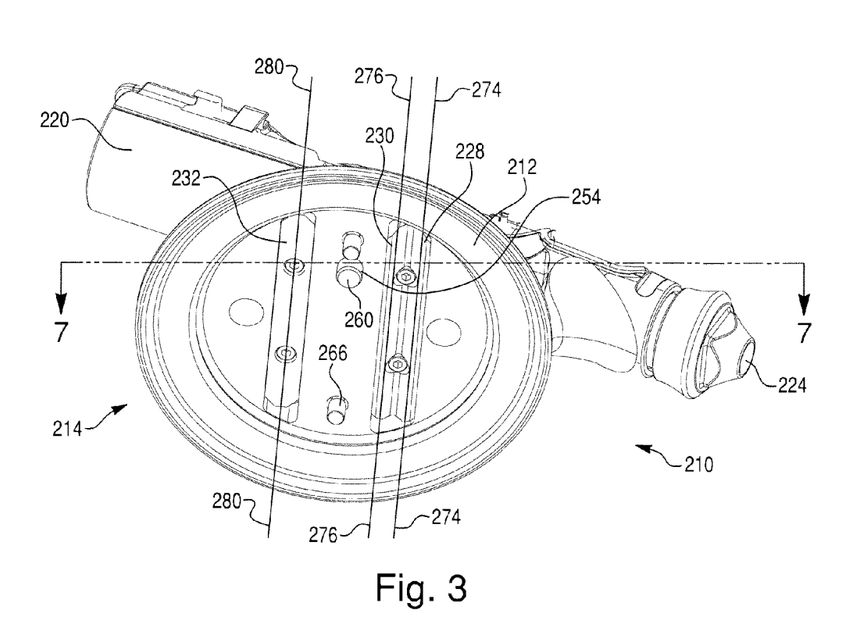
FIG. 3 is a perspective view of an embodiment of a first body member of the robotic surgical system of FIG. 1.

Referring to FIGS. 3 and 5, the positioning structure 214 of the first body member 212 can include a first surface 228, a second surface 230, and a third surface 232 (e.g., guide surfaces, contact surfaces, coupling surfaces, etc.). The first, second, and third surfaces 228, 230, 232 can be at least partially formed via precision cutting, stamping, grinding, polishing, lapping or another process for producing precise and accurate surface dimensions. In some embodiments, the first, second, and third surfaces 228, 230, 232 are individually or collectively formed on member(s), such as plates, that are fastened (e.g., screwed, pinned, glued, etc.) to the first body member 212. In other embodiments, one or more of the first, second, and third surfaces 228, 230, 232 are integrally formed with and on the first body member 212.

Figure 7:
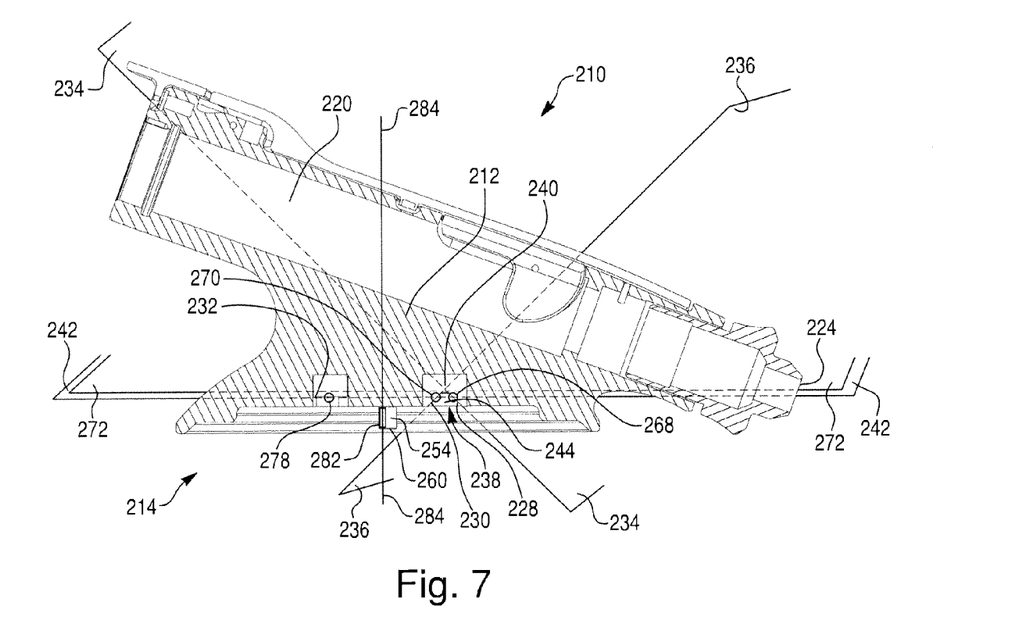
FIG. 7 is a sectional view of the first body member of FIG. 3, where the bottom portion of the sectional view is taken along line 7-7 of FIG. 3.

Referring to FIGS. 3, 5, and 7, the first, second, and third surfaces 228, 230, 232 preferably are each substantially rectangular and substantially planar. The first and second surfaces 228, 230 may define first and second planes 234, 236 (see FIG. 7) that intersect, forming an intersection 238 that is substantially V-shaped (when viewed from a plane that intersects and is normal to the first and second planes 234, 236). In contemplated embodiments, the first and second surfaces 228, 230 connect to form a vertex 240 of the V-shape. In other contemplated embodiments, the first and second surfaces 228, 230 do not connect, but the first and second planes 234, 236 defined by the first and second surfaces 228, 230 extend to form the vertex 240 of the intersection 238.

Preferably the third surface 232 defines a third plane 242 (see FIG. 7). According to an embodiment, the first, second, and third planes 234, 236, 242 are not coplanar or parallel. According to an exemplary embodiment, intersections 244 of the first, second, and third planes 234, 236, 242 form an isosceles triangular shape (when viewed from a plane intersecting the first, second, and third planes 234, 236, 242). In another embodiment, the isosceles triangular shape has the same size at any location along the intersections 244 (when viewed from a plane that intersects the first, second, and third planes 234, 236, 242 and that is orthogonal to each of the first, second, and third planes 234, 236, 242). In a preferred embodiment, the intersection 244 of the first and third planes 234, 242 is parallel to the intersection 244 of the second and third planes 236, 242. In another contemplated embodiment, intersections 244 of the first, second, and third planes 234, 236, 242 define a line collinear with the intersection 238 of the first and second planes 234, 236. In a preferred embodiment, the line is orthogonal to a plane that intersects the first, second, and third planes 234, 236, 242 and that is orthogonal to each of the first, second, and third planes 234, 236, 242.

It is contemplated that at least one of the first, second, and third surfaces 228, 230, 232 may not be planar, such as in an embodiment where the first and second surfaces 228, 230 are planar, and the third surface 232 defines a concave arc having a large radius of curvature. In still other contemplated embodiments, at least one of the first, second, and third surfaces 228, 230, 232 can be provided or formed on the second body member 216 and replaced on the first body member 212 by the corresponding structure from the second body member 216, which is described below.

Figure 4:
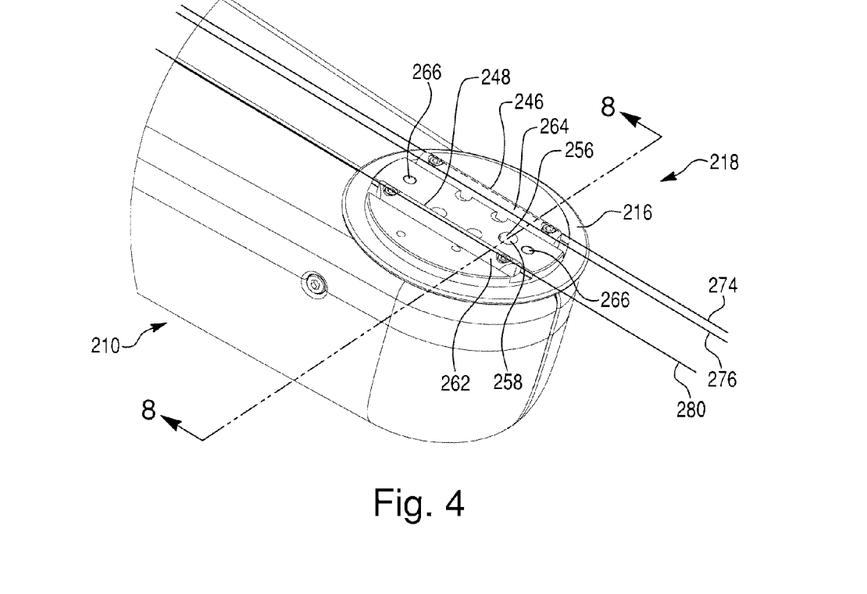
FIG. 4 is a perspective view of an embodiment of a second body member of the robotic surgical system of FIG. 1.
Figure 6:
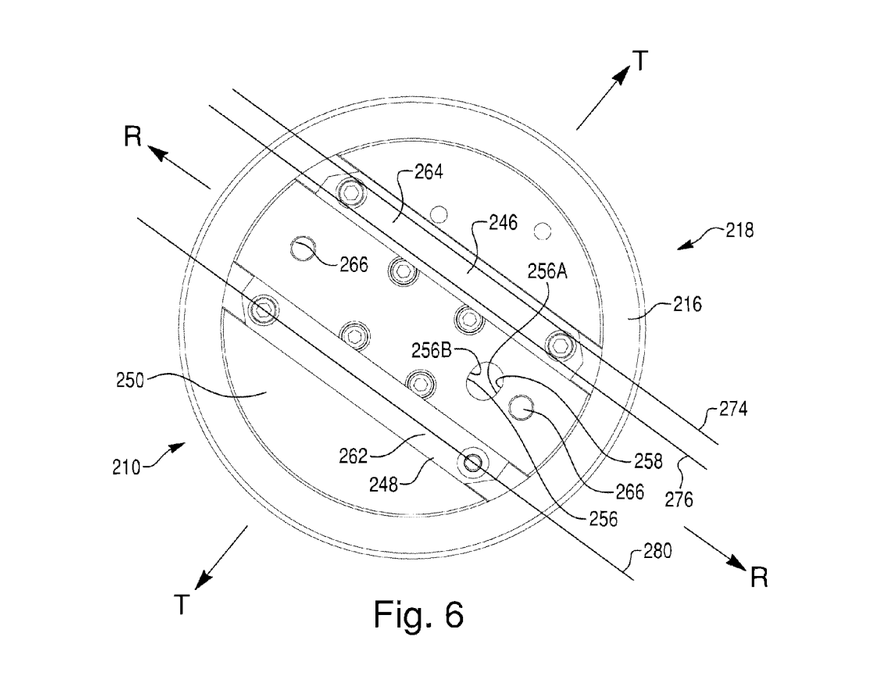
FIG. 6 is a plan view of the second body member of FIG. 4.
Figure 8:
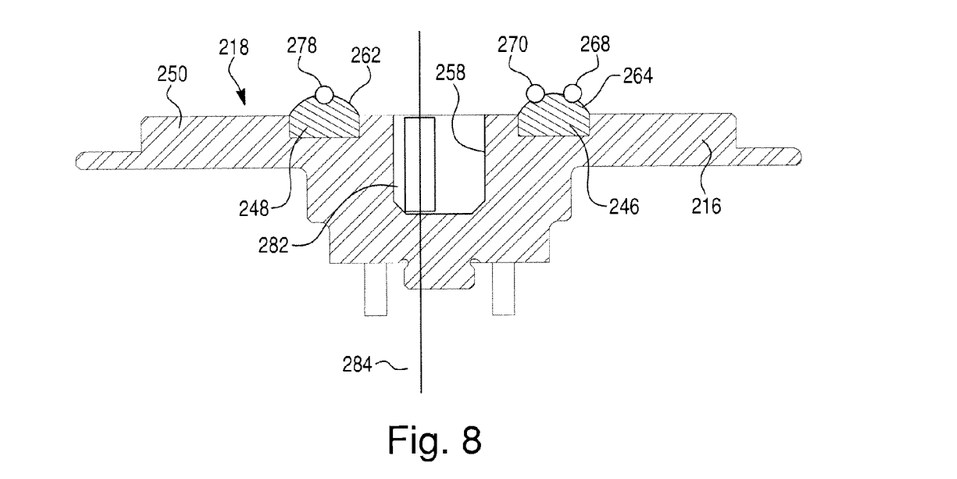
FIG. 8 is a sectional view of the second body member of FIG. 4, taken along line 8-8 of FIG. 4.

Referring to FIGS. 4, 6, and 8, the positioning structure 218 of the second body member 216 includes a first projection 246 and a second projection 248 (e.g., guide projections, contact projections, coupling projections, etc.). The first and second projections 246, 248 are preferably configured to extend away from an upper surface of a mount structure 250 of the second body member 216. However, the projections 246, 248 could be recessed below the upper surface of the mount structure 250. The first and second projections 246, 248 preferably are at least partially formed via a process for producing precise and accurate surface dimensions. The first and second projections 246, 248 can be formed as separable pieces that are fastened to the second body member 216. The first and second projections 246, 248 also could be integrally formed with and on the second body member 216.

The first and second projections 246, 248 preferably are semi-cylindrical or cylindrical (i.e., periphery having an arcuate portion), where the arcuate portions 262, 264 of the first and second projections 246, 248 are outwardly extending and preferably have substantially the same radius of curvature, although they could have different radii of curvature. The cross-sections of the first and second projections 246, 248 (see FIG. 8) preferably are substantially constant along longitudinal axes of each of the first and second projections 246, 248. The longitudinal axes of the first and second projections 246, 248 preferably extend in directions along the second body member 216 that are substantially parallel (e.g., less than a 5° angle of intersection and, more preferably, less than a 1° angle of intersection). In another embodiment, the longitudinal axes of the first and second projections 246 lie in the same plane but can be skewed relative to one another (i.e., not parallel). Despite the preferences stated above, the first and second projections 246, 248, may have semi-elliptical or otherwise contoured cross sections, may extend in directions that intersect, may have differently shaped cross-sections, and/or have cylindrical cross-sections with different radii of curvature.

Referring now to FIGS. 3-8, the positioning structure 214 of the first body member 212 further includes a third projection 254, and the positioning structure 218 of the second body member 216 further includes a fourth surface 256. The third projection 254 and fourth surface 256 can be at least partially formed via process(es) for producing precise and accurate surface dimensions. The third projection 254 can include a dowel fastened (e.g., screwed, pinned, glued, etc.) to the first body member 212, or the third projection 254 can be integrally formed with the first body member 212. The fourth surface 256 preferably is at least a portion of a sidewall of a slot 258 (e.g., elongated slot, aperture, precision slot, hole, etc.) formed in the second body member 216. The third projection 254 and the fourth surface 256 preferably extend longitudinally in directions that are substantially orthogonal to the third plane 242, defined by the third surface 232 (see generally fourth line 284 as shown in FIGS. 7-8). Despite the preference indicated above, the third projection 254 can be provided on the second body member 216 and the slot 258 can be provided on the first body member 212.

The third projection 254 preferably is cylindrical in shape. An end 260 of the third projection 254 extends away from the first body member 212. The end 260 can be, for example, rounded, beveled, chamfered, or otherwise contoured to facilitate entry into the slot 258.

The slot 258 can be formed in the mount structure 250 of the second body member 216 and configured to receive the third projection 254. The slot 258 preferably does not perfectly match the shape of the cross-section of the third projection 254, but is sized to substantially match at least some dimensions of the third projection 254, providing a controlled fit in at least one translational direction (e.g., a translational direction R-R that is orthogonal to the translational direction T-T). For reasons explained below, the slot 258 has a slightly larger size than the third projection 254 to accommodate slight positional inaccuracy in the translational direction T-T (see FIG. 6). As shown in the plan view of FIG. 6, the slot 258 preferably has an elongated shape, such as a rectangular shape or a "racetrack" shape having rounded ends. The precise shape is less important than the ability of the slot 258 to substantially constrain the third projection 254 in the translational direction R-R and permit freedom of positioning of the third projection 254 in the translational direction T-T. In a preferred embodiment, the fourth surface 256 of the slot 258 includes a surface 256A and a surface 256B (see FIG. 6) that are substantially parallel to one another and that are orthogonal to a plane that bisects the vertex 240 of the first and second planes 234, 236. For example, the surfaces 256A, 256B may comprise flat portions of the fourth surface 256. A distance between the surfaces 256A, 256B is substantially equivalent to a diameter of the third projection 254 or slightly greater than the diameter of the third projection 254 (e.g., by about 10 microns or less) to provide constraint in the translational direction R-R. Preferably the slot 258 is also sized to permit the third projection 254 to be positioned in the translational direction T-T within a predefined tolerance range that is no greater than the degree of precision required by the intended use of the device 210. For example, the elongated portion of the slot 258 preferably permits the third projection 254 to be positioned in the translational direction T-T within a tolerance range of less than about 1-2 mm. In this manner, the slot 258 provides constraint in one translational direction and accommodates positional inaccuracy within a predefined tolerance range in another translational direction.

Still referring to FIGS. 3-6, fastening structures 266 (see FIGS. 3-4) can be provided for facilitating clamping of the first and second body members 212, 216 together. In some embodiments, the fastening structures 266 include threaded apertures for threaded fasteners to extend therethrough. According to an exemplary embodiment, the threaded fasteners may be inserted into the fastening structures 266 in the first body member 212 and screwed into the second body member 216, clamping the first and second body members 212, 216 together. In such embodiments, a sufficient clamping force may be applied such that the first and second body members 212, 216 are rigidly fastened to each other, having substantially little or no relative rotation or movement during operation of a system of which the first and second body members 212, 216 are a part (e.g., robotic surgical system, precision coupling of shafts of laboratory test equipment, etc.).

According to an exemplary embodiment, the first, second, and third projections 246, 248, 254 and the first, second, third, and fourth surfaces 228, 230, 232, 256 of the first and second body members 212, 216 facilitate precision coupling (e.g., semi-kinematic coupling) of the first and second body members 212, 216, such that the first and second body members 212, 216 may be repeatedly unfastened and fastened back together in substantially the same relative position and orientation, and preferably also are configured to provide sufficient load carrying ability for the particular application in which the first and second body members 212, 216 will be used.

Referring to FIGS. 3-8 and 10, the first projection 246 extending from the second body member 216 is configured to contact the first and second surfaces 228, 230 of the first body member 212, when the first and second body members 212, 216 are fastened together. A first contact area 268 and a second contact area 270 are formed between the first projection 246 and the first and second surfaces 228, 230, respectively. The first and second contact areas 268, 270 are each substantially linear, and they preferably form substantially parallel first and second lines 274, 276 extending longitudinally (e.g., axially) along a portion of the lengths of the first projection 246 and the first and second surfaces 228, 230, when the first and second body members 212, 216 are coupled together. Without wishing to be bound by any theory, it is believed that this mode of contact substantially constrains in four degrees of freedom—two translational and two rotational.

The second projection 248 extending from the second body member 216 is configured to contact the third surface 232 of the first body member 212, when the first and second body members 212, 216 are fastened together. A third contact area 278 is formed between the second projection 248 and the third surface 232. The third contact area 278 is substantially linear and preferably forms a third line 280 extending along a portion of the lengths of the second projection 248 and third surface 232. Without wishing to be bound by any theory, it is believed that this mode of contact substantially constrains in one rotational degree of freedom. This mode of contact also accommodates positional inaccuracy of the second projection 248 because the third surface 232 will constrain the second projection 248, for example, even if the second projection 248 has slight positional inaccuracy in the translational direction T-T or is slightly rotated (e.g., skewed) relative to a line that is orthogonal to the third surface 232.

Certain relationships between the projection/surface interfaces, can be further advantageous. For example, in one embodiment, the first, second, and third lines 274, 276, 280 preferably are all substantially parallel. Furthermore, the first and second lines 274, 276 can define a fourth plane 272 (see FIG. 7), which preferably is substantially parallel to or coplanar with the third plane 242 (defined by the third surface 232). In one embodiment, the third line 280 is contained in a plane that is parallel to the fourth plane 272.

The third projection 254 extending from the first body member 212 is configured to be received in the slot 258 of the second body member 216 when the body members are fastened together. Because the slot 258 is elongated, it accommodates positional inaccuracy (described above) of the third projection 254 (and thus the first body member 212) in a translational direction (e.g., the translational direction T-T). As a result, the second body member 216 can engage with different first body members 212, even if each of the different first body members 212 has a unique (but within tolerance) positional accuracy in the translational direction T-T. However, the slot 258 constrains the first body member 212 in the translational direction R-R when the third projection 254 comes into contact with the fourth surface 256 (e.g., the surface 256A, the surface 256B) of the slot 258 to form a fourth contact area 282 (see FIG. 7). The fourth contact area 282 preferably is substantially linear and defines a fourth line 284 extending along a portion of the lengths of the third projection 254 and the fourth surface 256. The fourth line 284 preferably is substantially orthogonal to the third plane 242 defined by the third surface 232 and to the fourth plane 272 defined by the first and second lines 274, 276, which in turn are defined by the first and second contact areas 268, 270. Alternatively, depending on the dimensions of the third projection 254 and the slot 258, the third projection 254 may not contact the sidewalls of the slot 258 but instead may be located within the slot 258 with a small clearance between the third projection 254 and the sidewalls. In this embodiment, although there is no contact between the third projection 254 and the sidewalls, the fourth surface 256 still effectively constrains the third projection 254 because the third projection 254 is confined within the boundaries formed by the fourth surface 256 (e.g., the surfaces 256A, 256B) of the slot 258.

Without wishing to be bound by any theory, it is believed that the first, second, and third contact areas 268, 270, 278 together substantially constrain five degrees of freedom when the first and second body members 212, 216 are coupled— two translational degrees of freedom and three rotational degrees of freedom. It is believed that a third translational degree of freedom is substantially constrained by the fourth contact area 282 formed when the third projection 254 contacts or is disposed within the boundaries of the fourth surface 256 (e.g., the surface 256A, the surface 256B). It is further believed that the slight accommodation for translational positional inaccuracy between the third projection 254 and the fourth surface 256 helps to avoid over-constraining of the coupling of the first and second body members 212, 216.

The substantially linear contact areas (e.g., contact areas 268, 270, 278, 282) are preferred because they decrease the likelihood of deformation (elastic and plastic) during fastening of the first and second body members 212, 216, while still achieving a sufficiently accurate coupling (e.g., semi-kinematic coupling) for many precision applications. Relative to point contact, the substantially linear contact areas decrease the likelihood of deformation by reducing stress below the yield stress limits of the materials of the contacting components, although in applications that require lower load carrying ability, designs that include at least one point contact may also be employed. Suitable materials for the contacting components include any material that can be formed to create the contacting components (e.g., stainless steel, aluminum, titanium, plastic, ceramic, composite, etc.), provided the material has sufficient load bearing capability for the application in which the device 210 will be used.

Figure 9:
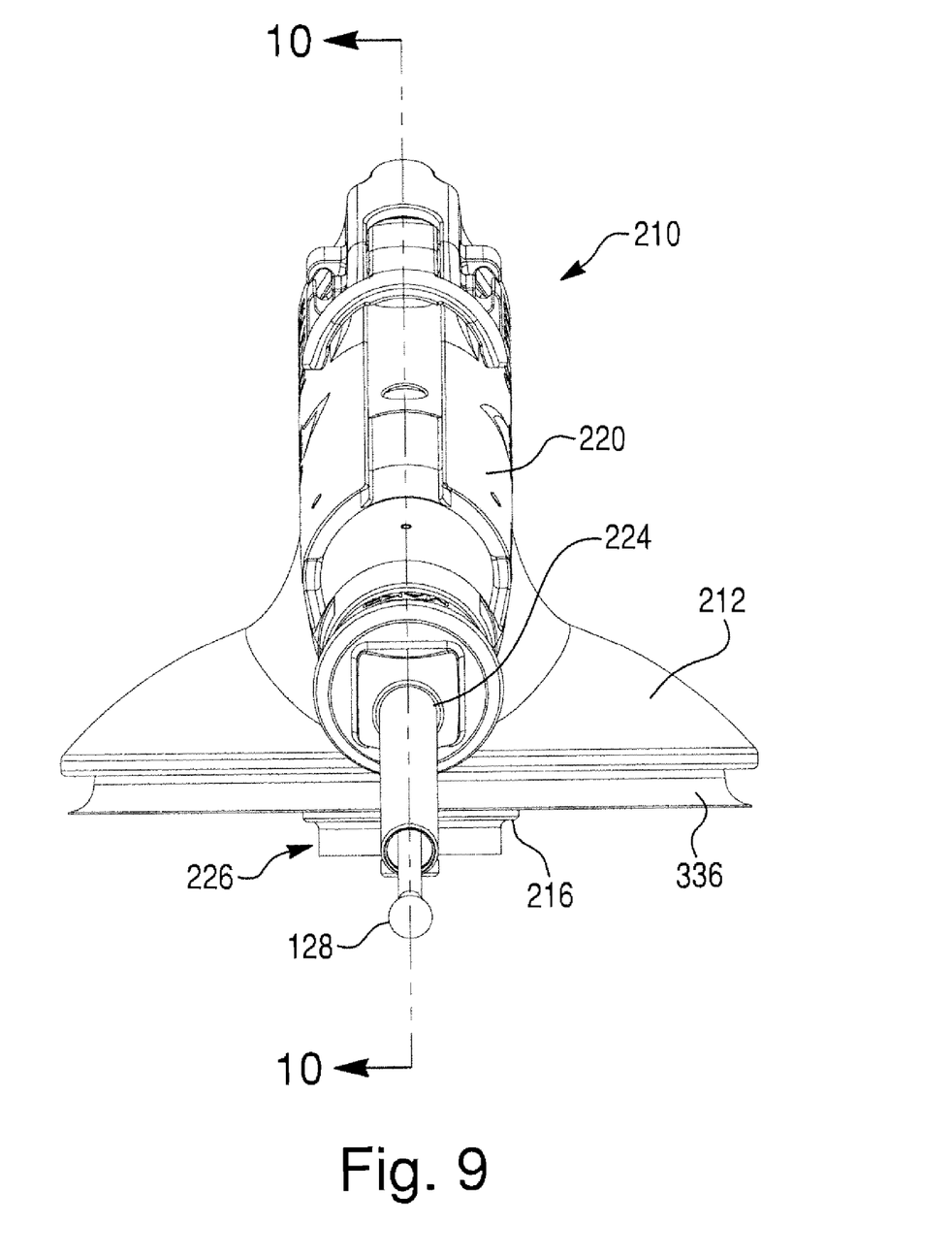
FIG. 9 is a front view of the first and second body members of FIGS. 3 and 4, with a tool attached thereto.
Figure 10:
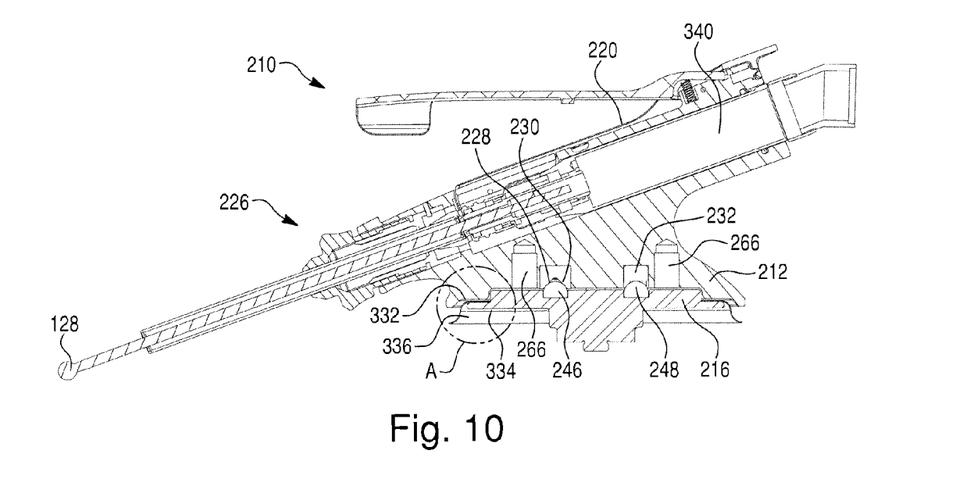
FIG. 10 is a sectional view of the first and second body members of FIGS. 3 and 4, taken along line 10-10 of FIG. 9, showing the tool and a drive.
Figure 11:
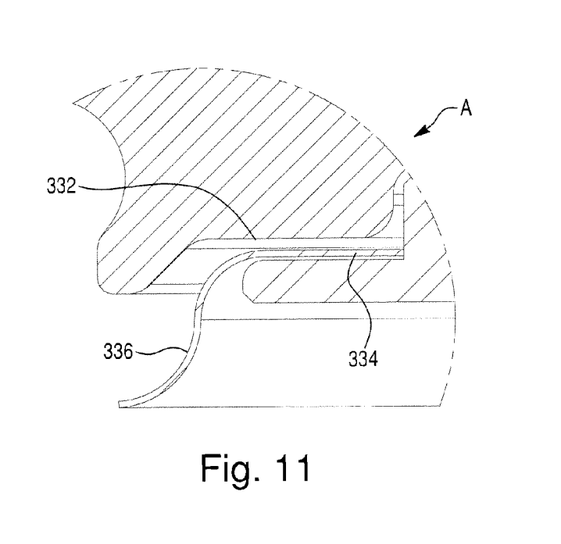
FIG. 11 is a partial sectional view of the first and second body members of FIGS. 3 and 4, showing a magnified view of circle A of FIG. 10.

Referring now to FIGS. 9-11, the device 210 further includes a first clamping surface 332 on the first body member 212 and a second clamping surface 334 on the second body member 216. The first clamping surface 332 and the second clamping surface 334 are configured to clamp a sheet material 336 therebetween. According to an exemplary embodiment, the sheet material 336 is relatively elastic (e.g., plastic) and does not substantially affect the accuracy of the semi-kinematic coupling. The sheet material 336 may serve as a sterile drape configured to protect surfaces of the end effector 210 or a robotic arm from dust, dirt, and other contaminants. In some embodiments, the sheet material 336 fully surrounds portions of the device 210 (e.g., the mount 126). In other embodiments, the sheet material 336 only partially surrounds portions of the device 210.

The construction and arrangements of the system devices and couplings, as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A device that can be assembled by coupling, comprising: first and second body members configured to be coupled relative to each other; and
a set of projections and surfaces associated with the first and second body members and configured to provide an interface between the first and second body members and position the first and second body members relative to each other via:
first, second, and third contact areas that are each substantially linear and are collectively configured to receive loads and position the first and second body members relative to each other in five degrees of freedom, and
a fourth contact area configured to limit positioning of the first and second body members relative to each other in a sixth degree of freedom in a first translational direction,
wherein the first and second contact areas are at least partially defined by contact between a first projection on one of the first and second body members and first and second surfaces on the other of the first and second body members,
wherein the third contact area is at least partially defined by contact between a second projection on the one of the first and second body members and a third surface on the other of the first and second body members, and
wherein the second projection is substantially in a shape of a semi-cylinder.

2. The device of claim 1, wherein the first, second, and third contact areas extend substantially parallel to one another.

3. The device of claim 1, wherein the first projection is substantially in a shape of a semi-cylinder.

4. The device of claim 1, wherein the first and second surfaces are substantially planar and extend along at least portions of a substantially V-shape.

5. The device of claim 1, wherein the third surface is substantially planar and extends in a direction that is substantially parallel to a plane containing the first and second contact areas.

6. The device of claim 1, wherein the fourth contact area is substantially linear and extends in a direction substantially orthogonal to a plane containing the first and second contact areas.

7. The device of claim 1, wherein the fourth contact area is at least partially defined by contact between a third projection on the other of the first and second body members and a fourth surface on the one of the first and second body members, wherein the third projection extends in a direction substantially orthogonal to a plane containing the first and second contact areas.

8. The device of claim 7, wherein the third projection is substantially in a shape of a cylinder.

9. The device of claim 8, wherein the fourth surface forms a portion of a side wall of an elongated slot configured to receive the third projection such that the third projection is disposed within a predefined tolerance range in the slot in a second translational direction.

10. The device of claim 1, wherein the first body member includes an end effector for a robotic arm, and the second body member includes a mount configured to connect the end effector to the robotic arm.

11. The device of claim 10, wherein the end effector includes a first clamping surface and the mount includes a second clamping surface, and the first and second clamping surfaces are configured to hold a sheet material therebetween when the end effector is coupled relative to the mount.

12. A device that can be assembled by coupling, comprising:
first and second body members configured to be coupled relative to each other; and
positioning structure configured to provide an interface between the first and second body members and position the first and second body members relative to each other in substantially six degrees of freedom, the positioning structure including
a first projection on one of the first and second body members and corresponding first and second surfaces on the other of the first and second body members, wherein contacts between the first projection and the first and second surfaces at least partially define first and second contact areas that each are substantially linear,
a second projection on the one of the first and second body members and a corresponding third surface on the other of the first and second body members, wherein contact between the second projection and the third surface at least partially defines a third contact area that is substantially linear,
wherein the first and second projections and the first, second and third surfaces are collectively configured such that the contacts between the first projection and the first and second surfaces and the contact between the second projection and the third surface position the first and second body members relative to each other in five degrees of freedom, and
a third projection on the other of the first and second body members and a corresponding fourth surface on the one of the first and second body members, wherein the third projection and the fourth surface are collectively configured such that contact between the third projection and the fourth surface limits positioning of the first and second body members relative to each other in a sixth degree of freedom in a first translational direction,
wherein each of the first and second projections is substantially in a shape of a semi-cylinder, and the first and second projections extend substantially parallel to one another.

13. The device of claim 12, wherein the first and second surfaces are substantially planar and extend along at least portions of a substantially V-shape.

14. The device of claim 12, wherein the third surface is substantially planar and extends in a direction that is substantially parallel to a plane containing the first and second contact areas.

15. The device of claim 12, wherein the third projection is substantially in a shape of a cylinder.

16. The device of claim 15, wherein the third projection extends in a direction substantially orthogonal to a plane containing the first and second contact areas.

17. The device of claim 12, wherein contact between the third projection and the fourth surface at least partially defines a fourth contact area that is substantially linear and extends in a direction substantially orthogonal to a plane containing the first and second contact areas.

18. The device of claim 12, wherein the fourth surface forms a portion of a side wall of an elongated slot configured to receive the third projection such that the third projection is disposed within a predefined tolerance range in the slot in a second translational direction.

19. The device of claim 12, wherein the first body member includes an end effector for a robotic arm, and the second body member includes a mount configured to connect the end effector to the robotic arm.

20. The device of claim 19, wherein the end effector includes a first clamping surface and the mount includes a second clamping surface, and the first and second clamping surfaces are configured to hold a sheet material therebetween when the end effector is coupled relative to the mount.

* * * * *